(12) United States Patent
Kronenberg et al.

(10) Patent No.: US 11,344,755 B2
(45) Date of Patent: May 31, 2022

(54) NASAL AIR FILTER

(71) Applicants: Sandy Kronenberg, West Bloomfield, MI (US); Adam Kehres, South Lyon, MI (US)

(72) Inventors: Sandy Kronenberg, West Bloomfield, MI (US); Adam Kehres, South Lyon, MI (US)

( * ) Notice: Subject to any disclaimer, the term of this patent is extended or adjusted under 35 U.S.C. 154(b) by 355 days.

(21) Appl. No.: 16/415,225

(22) Filed: May 17, 2019

(65) Prior Publication Data
US 2019/0269946 A1   Sep. 5, 2019

Related U.S. Application Data

(63) Continuation of application No. 14/608,827, filed on Jan. 29, 2015, now Pat. No. 10,322,304.

(51) Int. Cl.
| | | |
|---|---|---|
| *A62B 23/06* | (2006.01) | |
| *A61M 16/10* | (2006.01) | |
| *A62B 18/08* | (2006.01) | |

(52) U.S. Cl.
CPC .......... *A62B 23/06* (2013.01); *A61M 16/105* (2013.01); *A62B 18/088* (2013.01)

(58) Field of Classification Search
CPC ..... A62B 23/06; A62B 18/088; A61M 16/105
See application file for complete search history.

(56) References Cited

U.S. PATENT DOCUMENTS

| | | | | |
|---|---|---|---|---|
| 3,884,223 A | * | 5/1975 | Keindl .................. | A62B 23/06 128/206.11 |
| 6,607,134 B1 | * | 8/2003 | Bard ..................... | G04B 47/00 235/462.44 |
| 2004/0147954 A1 | * | 7/2004 | Wood ................... | A61M 29/00 606/199 |
| 2009/0007919 A1 | * | 1/2009 | Dolezal ................. | A62B 7/10 128/206.11 |
| 2016/0121144 A1 | * | 5/2016 | Hyde ................... | A62B 23/025 128/206.11 |
| 2016/0256715 A1 | * | 9/2016 | Chao .................... | A62B 23/06 |

* cited by examiner

*Primary Examiner* — Timothy A Stanis

(57) ABSTRACT

An air filter configured to be inserted into a nasal cavity of a user, the filter including an outer shell and an inner shell that are connectable, an electronic filter provided between the outer and inner shells, and a flat battery connected to the electronic filter and provided between the outer and inner shells.

7 Claims, 4 Drawing Sheets

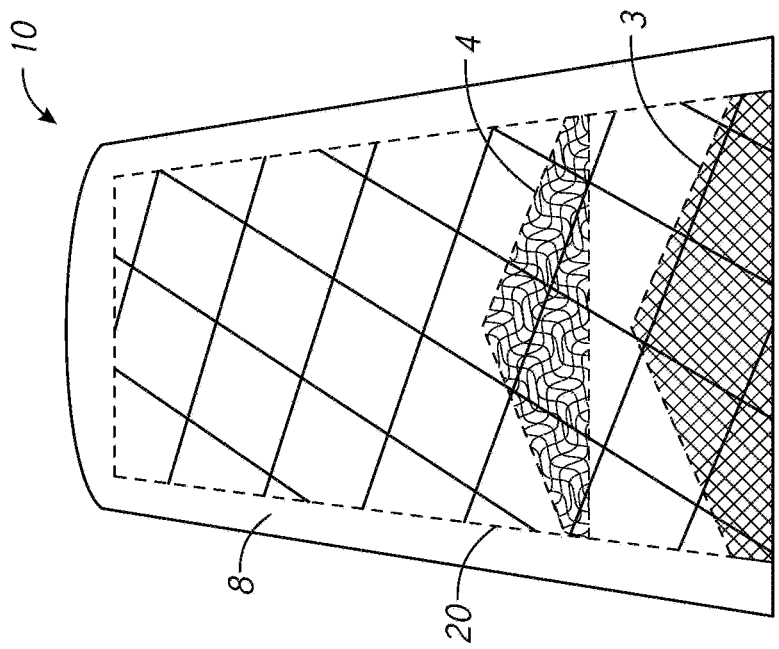
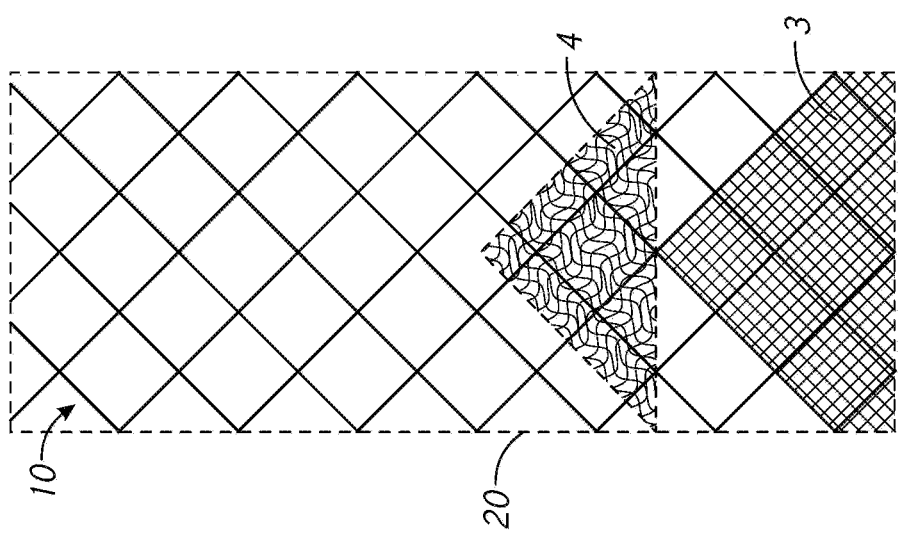

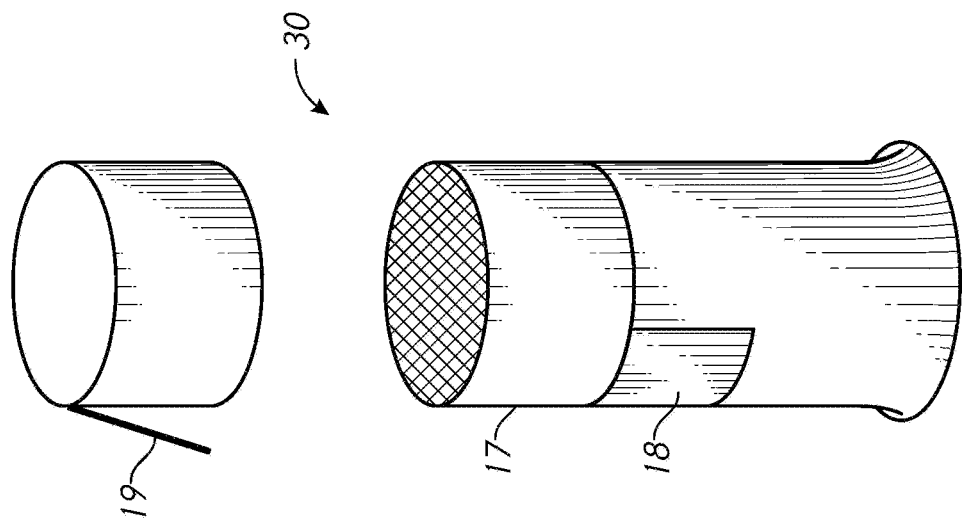
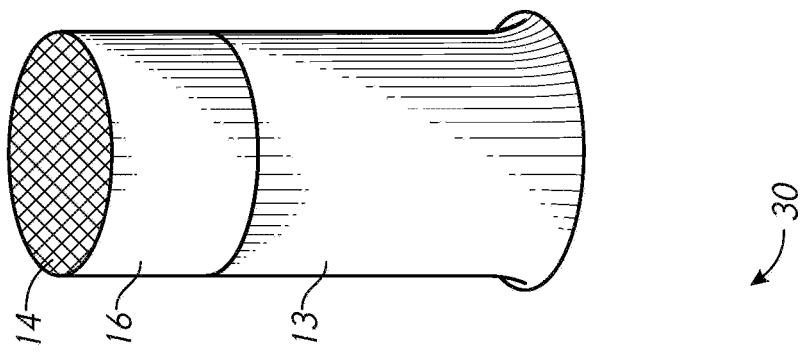
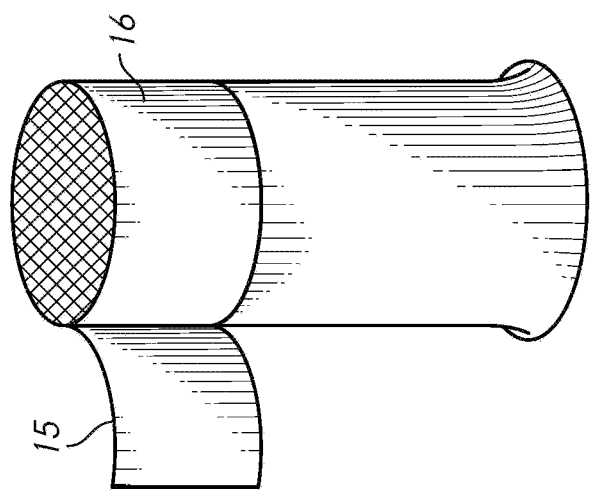

NASAL AIR FILTER

CROSS-REFERENCE TO RELATED APPLICATION(S)

This application is a Continuation Application of prior U.S. patent application Ser. No. 14/608,827 filed Jan. 29, 2015, whose entire disclosure is hereby incorporated by reference.

FIELD OF THE INVENTION

This invention relates generally to an improved, wearable air filtration system, more particularly to a tubular filter inserted into the nostrils of the wearer for filtering smog and other airborne particles.

BACKGROUND OF THE INVENTION

The frequency of Ozone Alerts worldwide is increasing at an alarming rate and the health concerns are quite conclusive with more and more research reports being issued. These Ozone Alerts as announced by the media are actually Smog Alerts. The warnings are that the very old and the very young should avoid going outdoors if the air quality is very poor. Photochemical smog (summer smog) is caused by the action of sunlight on a mixture of hydrocarbons and oxides of nitrogen created mostly by automobile and industrial exhaust emissions. This smog contains secondary pollutants such as ozone, aldehydes and fine particles. Of these "secondary pollutants", ozone is used as an indicator as it is easily and accurately monitored, and directly proportional to overall smog levels. When we refer to ozone, we are referring only to tropospheric ozone, not to be confused with stratospheric ozone, which forms a layer around the earth, protecting it from the rays of the sun. Tropospheric ozone is produced by the action of light and the chemical bonding of volatile organic compounds (VOCs) and nitrogen oxides (NOx). Thus "SMOG" and "Ozone" alerts have become synonymous. The severity of smog in an urban area is usually assessed by measuring ground-level ozone. Tropospheric ozone ($O_3$) is found as a ground-level polluting gas.

Smog, formed mainly above urban centers, is composed mainly of tropospheric ozone ($O_3$); primary or coarse particulate matter such as soot, pollen and dust; and secondary or fine particulate matter such as sulphur oxides, volatile organic compounds, nitrogen oxides (NOx) and ammonia gas. As described by the EPA, coarse particles are larger than 2.5 micrometers and smaller than 10 micrometers in diameter, and fine particles are thus 2.5 micrometers and smaller.

As a result of heat from the rays of the sun, the concentration of ground-level ozone is highest in urban centers in the summer. Weather conditions also affect ozone formation; masses of stagnant air can hold pollutants at ground level for several days.

Many people have resorted to wearing masks to filter out the primary and secondary particulate matter. The masks are needed by those who have already developed respiratory issues due to the smog. Many others don the masks prophylactically. Regardless of the reason for wearing the masks—most people do not realize that the masks are often not sufficient filters. Most face masks are only 20-30% effective (1) because of the inadequate filtration media. There are facemasks known as N95 and N100 that employ a much more effective media but often people are not wearing the facemasks appropriately which servers to lower the efficacy. Many people are not wearing the appropriate clips and are not aware of the gaps in these face masks that don't properly conform the to the users face.

SUMMARY OF THE INVENTION

What is described herein is a method of using one or more filtration methods to capture primary and secondary particulate matter. This method is employing a much more reliable system that conforms much closer to the airflow openings. Essentially, the simple tubular design removes many of the possible errors seen from facemasks. Once inserted into the nostril, the airflow is almost entirely through the filter. Simple nasal air filters are already known in the art; for examples, U.S. Pat. Nos. 8,347,885, 6,971,388, 6,701,924, 5,117,820, and 4,220, 150. The described invention seeks to improve upon these simple designs through a variety of means, described herein. Several embodiments are described, including a preferred embodiment, as well as alternative uses and accessories which may be included with any embodiment.

In a preferred embodiment, a two-stage filter system is used, including a microfiber filter and a nanofiber filter used in series, with the nanofiber filter preferably located downstream of the microfiber filter. As stated previously, it is best to utilize a two-stage filter system in order to best capture the different sized particles without restricting air flow. The two-stage filter system is contained within a flexible housing. The housing may be constructed using any number of flexible materials. In an exemplary embodiment, the housing will be able to dilate or expand and contract when being inserted or removed. When fully dilated, the housing will act to completely fill the user's nostril, thus forcing all breathed air to pass through the filter system before entering the user's lungs. When contracting, the filter system will contract in direct correlation to the housing itself.

The primary or coarse particulate matter is filtered best by natural human mucus linings in the nose, throat, and trachea. However, primary particulates can also be filtered through a microfiber filtration system. This can include a plurality of microfibers arranged to collect primary or coarse particulate matter as the air is breathed in through the filter. An example of a preferred microfiber filter is described in U.S. Pat. No. 6,924,028.

The secondary or fine particulate matter is filtered best by a nanofiber filtration system. The human respiratory system is not equipped to naturally filter fine particles, which can enter the lungs. Once in the lungs, these particles are difficult to expel and thus end up causing long term problems. The nanofiber filtration system can include a plurality of nanofibers arranged to collect secondary particulate matter as the air is breathed in through the filter, preferably at a location downstream of the microfiber filtration system. Finally, a connecting piece along the septum of the nose may be included to connect each nostril filter for ease of insertion and removal, and to provide stability during heavy breathing or sneezing. An example of a preferred nanofiber filter is described in U.S. Pat. No. 8,523,971.

Alternatively, an electronic filter component, composed of electrically conducting and chargeable plates which attract the particulate matter, is powered by a battery. An example of an electronic air filter is described in U.S. Pat. No. 5,232,478. The battery may be in the form of a traditional battery or a new method which wraps the battery around the tubular design. For example, one positive electrode, Lithium, is quite flexible and can be made into flat tape that could wrap around an inner-core of the tubular design. The filter would employ the chargeable plates, the small battery, and potentially a small circuit board for effective control of power administered to the plates.

In addition to leveraging a multitude of filtering technologies, feedback may also be provided to the wearer by employing contact closures and radio frequency technology (including but not limited to WiFi and Bluetooth) in the form of a small RFID tag to communicate with a portable electronic device, such as a smartphone, tablet, or personal computer. This communication can allow tracking of the location of the user and the amount of time the device is worn, providing valuable information which can help the user. A simple equation can be used to calculate the deterioration of the filter as a function of time in use, giving an estimation of when the filter should be replaced, depending on the quality of outside air being breathed. By using a centralized air quality service such as NOAA Air Quality Forecast Guidance System, a smartphone application can compare the user data with the centralized data service. Therefore a correlation can be drawn that would show the amount of smog and make a better estimate of the life of the filter and the amount of particulate matter that the user has avoided breathing in. If the device has reusable filters, a notification can be given to the user to clean the filters and/or replace them.

Alternatively, the filter can be fitted with an onboard air sensor downstream of the filter, which can relay information as to the air quality passing through the filter in real time to a wearer's cell phone, tablet, or personal computer through the RFID tag. This information can tell the user how well the filter is functioning and when it would be time to replace or clean the filters. Such information can be used in tandem with NOAA Air Quality Forecast Guidance System information, and provide alerts that a current filter is or is not currently effective in filtering out harmful particles.

Another use of the nasal filters is to improve air flow for the wearer for sporting activities and/or during periods of nasal congestion such as during the course of a flu or cold. The filter serves to dilate the nasal cavity much in the same way the popular Breath-Right® strips but without the flaws associated with exteriorly worn product. The breath-right strips have an adhesive attached to a flexible support that attempts to dilate a user's nasal passage but this adhesive is temporary and therefore the product must be discarded, as seen in U.S. Pat. No. 7,013,889. Furthermore, because the strips are externally applied, the unpredictability of the adhesive creates many potential failure modes. The proposed method of flexible expanding tube worn on the interior serves to keep the nasal passage open and dilated for a prolonged period of time and does not have the limitation of the adhesive's short life-span.

BRIEF DESCRIPTION OF THE DRAWINGS

The accompanying drawings, which are incorporated in and constitute a part of this specification, illustrate an implementation of the invention and, together with the description, serve to explain the advantages and principles of the invention. In the drawings.

FIG. 3A depicts an embodiment of a filter in a compressed state;

FIG. 3B depicts an embodiment of a filter in an expanded, operational state;

FIG. 4 depicts a block diagram of the components of the electronic filter and power source consistent with the principles of the present invention;

FIG. 5 depicts a block diagram of the components of the contact closure, radio frequency transmitter and power source consistent with the principles of the present invention.

DETAILED DESCRIPTION OF THE DRAWINGS

The following detailed description of the invention refers to the accompanying drawings. Although the description includes exemplary implementations, other implementations are possible, and changes may be made to the implementations described without departing from the spirit and scope of the invention. The following detailed description does not limit the invention. Instead, the scope of the invention is defined by the appended claims. Wherever possible, the same reference numbers will be used throughout the drawings and the following description to refer to the same or like parts.

Figure 1:
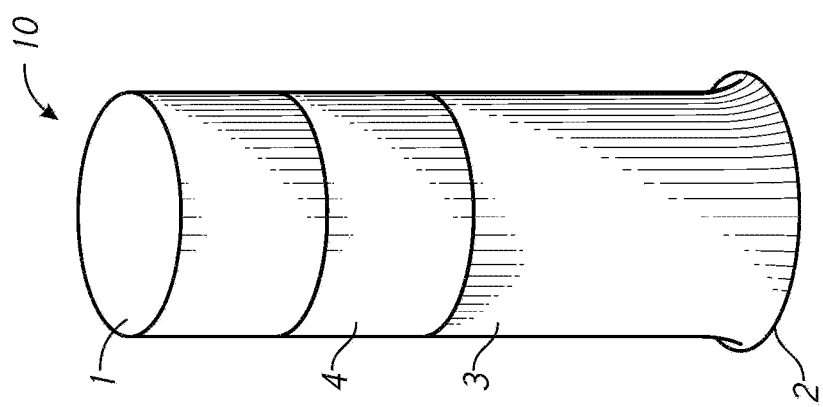
FIG. 1 is a block diagram of the filter system in a manner consistent with the principle of the present invention.

FIG. 1 shows a block diagram represents a nasal filter 10. A top portion 1 is located in the nasal cavity, while a bottom portion 2 is located near the nasal tip. Both the top portion 1 and the bottom portion 2 can be manufactured to be rigid with a soft, deformable covering, or be constructed entirely of flexible material. As seen in FIG. 1, the filter 10 can be predominantly tubular shaped, however, more precise designs conforming to shapes of nostrils are obvious. The base of the filter 10 can flare out to prevent the filter 10 from get pushed too far up into the nasal cavity—hence allowing the filter 10 to be easily removed or to prevent it from causing damage. The unfiltered air enters the filter 10 through the bottom portion 2 and traverses a single or multi stage filtration media 3, 4, represented in FIG. 6. In an exemplary embodiment, the coarse filter material 3 is located upstream of the fine filter material 4, however it is possible to have the filter materials 3, 4 in either order. Furthermore, it would be obvious to one of ordinary skill in the art to combine the filter materials into a single component.

Figure 2:
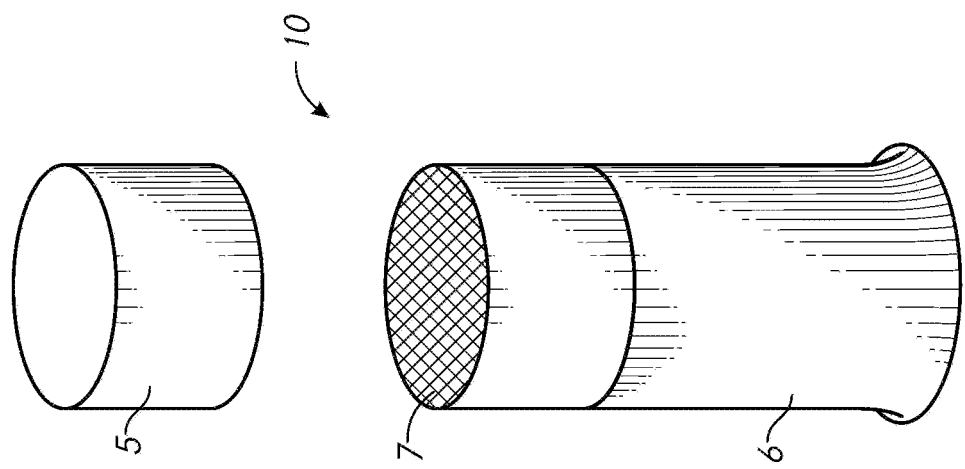
FIG. 2 depicts a block diagram of the components of the filter system depicted in FIG. 1.

FIG. 2 shows an alternate embodiment of a multi-piece filter 10. The filter 10 may be comprised of one or more components 5, 6 that are fitted together to provide a smooth surface for the inhaled and exhaled air to traverse without abrupt edges that would cause unwanted noise. As an example, the top component 5 can hold the filter material 7 in place whether it is electrostatic or electronic. The bottom component 6 is where the filter material 7 is mounted. As per the diagram, the actual filter material 7 would be locked into place by fitting the two components 5, 6 together. The two components 5, 6 may be fused if the filter 10 is disposable. Another scenario is to allow separation of the top component 5 and the bottom component 6 in order to access and change or clean the filter material 7. The filter material 7 itself may either be washed, cleaned, replaced, or removed (in the case where there are many modes of filtration, airflow is a concern, or one mode is removed).

FIG. 3A displays an exemplary filter housing design. In this design, the housing 20 of the filter 10 is malleable and may be compressed and elongated for insertion, and shortened and dilated for operation. The housing or shell 20 is shown in an elongated state in FIG. 3A. While elongated, the one or multiple filtration media 3, 4 may alter shape by collapsing radially inward. Alternatively, a rigid inner wall 8 may hold the one or multiple filtration media 3, 4 fixedly in place, while an outer housing or shell 20 remains deformable for insertion into the nostril and comfort while in place.

FIG. 3B shows the housing or shell 20 in a dilated state. When dilated, the filter 10 acts to expand the nostril of the wearer, allowing an increased amount of air to pass through the filter 10. The increased amount of air acts to offset the reduction of flow pressure generated by the presence of one or multiple filtration media 3, 4. The one or multiple filtration media 3, 4 can be located at any length along the inside of the housing or shell 20, and may be separated by any distance. The housing or shell 20 may also taper at the proximal nasal cavity end in order to fit a variety of user nostril sizes, and may flare at the distal nostril end in order to avoid being pushed too far into a user's nasal cavity.

FIG. 4 shows an alternate embodiment of an electronic filter 30. The electronic filter 30 is comprised of an outer shell assembly 13, housing charging plates 14 which attract particles when charged by a battery cell 15. The plates 14 are arranged within the outer shell assembly 13, preferably near the proximal top portion of the outer shell assembly 13. The outer shell assembly 13 fits over an inner core 16 having a battery cell 15. The battery cell 15 is an electrode having a positive end and a negative end, which wraps around the inner core 16 of the electronic filter 30. The inner core 16 may be constructed of a rigid, nonconducting material, so as to properly hold the battery cell 15 in place and not transmit the electric charge through the entire filter 30. When the outer shell assembly 13 and the inner core 16 are fitted together, the battery cell 15 is activated and a charge is sent through the charging plates 14, acting to attract and collect particles from incoming air. The outer shell assembly 13 may be constructed of a soft, pliable, nonconducting material, so as to avoid transmitting the electric charge into the user.

FIG. 5 shows another alternative embodiment of an electronic filter 30, comprising a battery cell 17, an RFID transmitter tag 18, and a contact closure 19. The battery cell 17 may be a small watch battery, as is well known in the art, or a battery cell 15 as described in FIG. 4. The RFID transmitter tag 18 can be attached to an inner core 16 as described in FIG. 4, or may be integrated into the housing or shell 20 as described in FIG. 3A. The RFID transmitter tag 18 would allow filter media such as the charged plates 14 or one or multiple filter media 8, 9 to communicate with a user's personal electronic device such as a cell phone or personal computer, relaying such information as filter life or air quality. The contact closure 19 can be a simple switch which is activated when the filter assembly 40 is placed inside a user's nostril. This would also communicate with the user's personal electronic device through the RFID transmitter tag 18 to relay important information.

Figure 6:
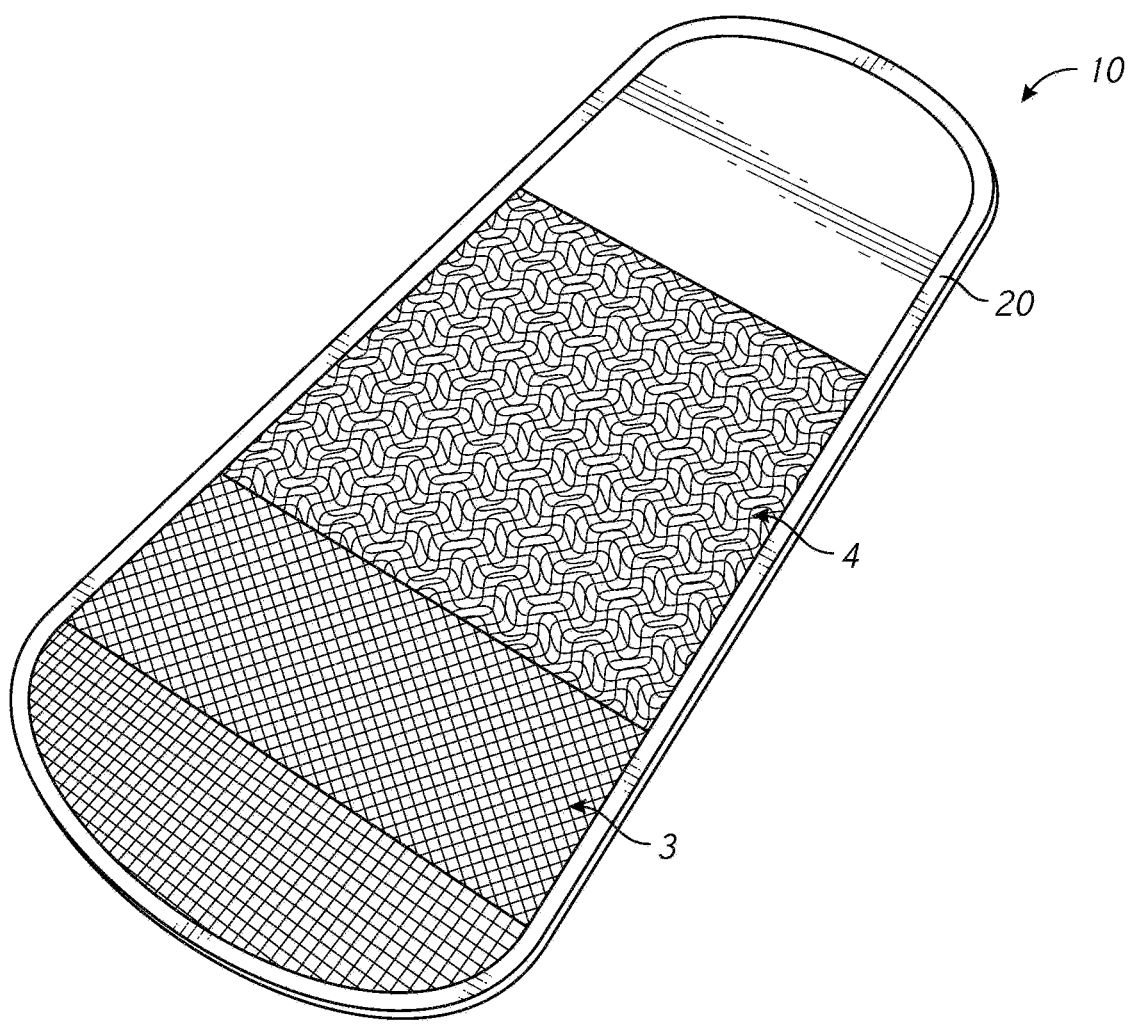
FIG. 6 depicts a cut away view of a filter design, showing a two stage filter.

FIG. 6 shows the cross section of an exemplary filter. In this example, the entire filter 10 is malleable, and can be deformed for insertion into a user's nostril. The outer housing 20 may be composed of such material as foam or soft rubber, and will encase one or more filter materials, including potentially a coarse, microfiltration element 3 and a fine, nanofiltration element 4. These filter materials 3, 4 may be a foam-like substance as well, allowing deformation without sacrificing filtration ability.

What is claimed is:

1. An air filter configured to be inserted into a nasal cavity of a user, the air filter comprising:
   an outer shell, the outer shell comprising an electronic filter element;
   an inner core removably inserted into the outer shell; and
   a battery strip configured to wrap circumferentially around the inner core;
   wherein the inner core selectively connects the battery strip to the electronic filter element to produce an electrical current through the electronic filter element when the inner core is inserted into the outer shell.

2. The air filter of claim 1, wherein the outer shell is a flexible material.

3. The air filter of claim 2, wherein the battery strip is a lithium battery strip, having a positive end and a negative end.

4. The air filter of claim 3, wherein the electronic filter element comprises a plurality of electrically conducting plates.

5. The air filter of claim 4, further comprising a radio frequency transmitter, wherein the radio frequency transmitter is operably connected to the electronic filter element and the battery strip.

6. The air filter of claim 5, further comprising a contact closure attached to the outer shell.

7. The air filter of claim 6, wherein the radio frequency transmitter communicates to a portable electronic device.

* * * * *